United States Patent [19]  
Conrow et al.

[11] 4,102,917  
[45] Jul. 25, 1978

[54] SUBSTITUTED PHENYL NAPHTHALENESULFONIC ACIDS

[75] Inventors: Ransom Brown Conrow, Pearl River; Seymour Bernstein, New City, both of N.Y.

[73] Assignee: American Cyanamid Company, Stamford, Conn.

[21] Appl. No.: 802,340

[22] Filed: Jun. 1, 1977

[51] Int. Cl.$^2$ .................. C07C 143/36; A61K 31/185
[52] U.S. Cl. .................... 260/506; 260/454; 260/543 R; 424/315
[58] Field of Search ........................................ 260/506

[56] References Cited

U.S. PATENT DOCUMENTS

| | | | |
|---|---|---|---|
| 2,070,127 | 2/1937 | Hilger et al. | 260/506 |
| 4,051,176 | 9/1977 | Bernstein et al. | 260/506 |

FOREIGN PATENT DOCUMENTS

| | | | |
|---|---|---|---|
| 123,693 | 4/1900 | Fed. Rep. of Germany | 260/506 |
| 817,463 | 6/1951 | Fed. Rep. of Germany | 260/506 |
| 71,540 | 1/1916 | Switzerland | 260/506 |

Primary Examiner—Joseph E. Evans  
Attorney, Agent, or Firm—Jack W. Richards

[57] ABSTRACT

Trinaphthalene trisulfonic acid and mono naphthalene trisulfonic acid-dibenzene dicarboxylic acid salts of di(carbonylimino) and mono(thioureido) trisubstituted phenyl compounds useful as complement inhibitors.

4 Claims, No Drawings

SUBSTITUTED PHENYL NAPHTHALENESULFONIC ACIDS

DESCRIPTION OF THE INVENTION

This invention is concerned with compounds of the formula:

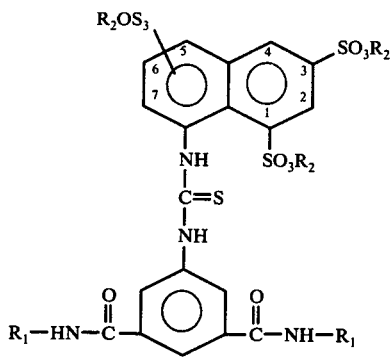

wherein $R_1$ is selected from the group consisting of

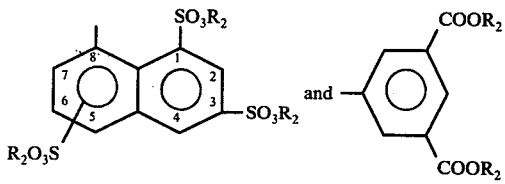

wherein $R_2$ is selected from the group consisting of alkali metal; and the pharmaceutically acceptable salts thereof A preferred embodiment of the instant invention consists of these compounds wherein $R_1$ is selected from the group consisting of

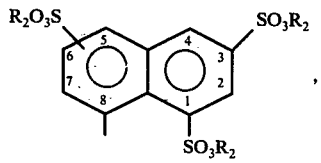

wherein $R_2$ is as previously defined.

The compounds of the present invention may be prepared by treating 8,8'-[(5-amino-m-phenylene)bis(carbonylimino)]di-1,3,6-naphthalenetrisulfonic acid hexaalkali metal salt with 8-isothiocyanato-1,3,6-naphthalenetrisulfonic acid trialkali metal salt in water for 23 hours. The product is isolated as the nonaalkali metal salt from 80% aqueous ethanol. Additionally, 5,5'-[5-amino-1,3-phenylenebis(carbonylimino)]diisophthalic acid tetraalkali metal salt is treated by stirring with 8-isothiocyanato-1,3,6-naphthalenetrisulfonic acid trialkali metal salt in water for 18 hours. The product is isolated as the heptaalkali metal salt from 66% aqueous ethanol.

The term "complement" refers to a complex group of proteins in body fluids that, working together with antibodies or other factors, play an important role as mediators of immune, allergic, immunochemical and/or immunopathological reactions. The reactions in which complement participates take place in blood serum or in other body fluids, and hence are considered to be humoral reactions.

With regard to human blood, there are at present more than 11 proteins in the complement system. These complement proteins are designated by the letter C and by number: C1, C2, C3 and so on up to C9. The complement protein C1 is actually an assembly of subunits designated C1q, C1r and C1s. The numbers assigned to the complement proteins reflect the sequence in which they become active, with the exception of complement protein C4, which reacts after C1 and before C2. The numerical assignments for the proteins in the complement system were made before the reaction sequence was fully understood. A more detailed discussion of the complement system and its role in body processes can be found in, for example, Bull. World Health Org., 39, 935–938 (1968); Ann. Rev. Medicine, 19, 1–24 (1968); The John Hopkins Med. J., 128, 57–74 (1971); Harvey Lectures, 66, 75–104 (1972); The New England Journal of Medicine, 287, 452–454; 489–495; 545–549; 592–596; 642–646 (1972); Scientific American, 229, (No. 5), 54–66 (1973); Federation Proceedings, 32, 134–137 (1973); Medical World News, October 11, 1974, pp. 53–58; 64–66; J. Allergy Clin. Immunol., 53, 298–302 (1974); Cold Spring Harbor Conf. Cell Proliferation 2/Proteases Biol. Control/229–241 (1975); Annals of Internal Medicine, 84, 580–593 (1976); "Complement: Mechanisms and Functions," Prentice-Hall, Englewood Cliffs, N.J. (1976).

The complement system can be considered to consist of three sub-systems: (1) a recognition unit (C1q) which enables it to combine with antibody molecules that have detected a foreign invader; (2) an activation unit (C1r, C1s, C2, C4, C3) which prepares a site on the neighboring membrane; and (3) and attack unit (C5, C6, C7, C8 and C9) which creates a "hole" in the membrane. The membrane attack unit is non-specific; it destroys invaders only because it is generated in their neighborhood. In order to minimize damage to the host's own cells, its activity must be limited in time. This limitation is accomplished partly by the spontaneous decay of activated complement and partly by interference by inhibitors and destructive enzymes. The control of complement, however, is not perfect, and there are times when damage is done to the host's cells. Immunity is therefore a double-edged sword.

Activation of the complement system also accelerates blood clotting. This action comes about by way of the complement-mediated release of a clotting factor from platelets. The biologically active complement fragments and complexes can become involved in reactions that damage the host's cells, and these pathogenic reactions can result in the development of immune-complex diseases. For example, in some forms of nephritis, complement damages the basal membrane of the kidney, resulting in the escape of protein from the blood into the urine. The disease disseminated lupus erythematosus belongs in this category; its symptoms include nephritis, visceral lesions and skin eruptions. The treatment of diphtheria or tetanus with the injection of large amounts of antitoxin sometimes results in serum sickness, an immune-complex disease. Rheumatoid arthritis also involves immune complexes. Like disseminated lupus erythematosus, it is an autoimmune disease in which the disease symptoms are caused by pathological effects of the immune system in the host's tissues. In summary, the complement system has been shown to be involved with inflammation, coagulation, fibrinolysis, antibody-antigen reactions and other metabolic processes.

In the presence of antibody-antigen complexes the complement proteins are involved in a series of reactions which may lead to irreversible membrane damage if they occur in the vicinity of biological membranes. Thus, while complement constitutes a part of the body's defense mechanism against infection it also results in inflammation and tissue damage in the immunopathological process. The nature of certain of the complement proteins, suggestions regarding the mode of complement binding to biological membranes and the manner in which complement effects membrane damage are discussed in Annual Review in Biochemistry, 38, 389 (1969).

A variety of substances have been disclosed as inhibiting the complement system, i.e., as complement inhibitors. For example, the compounds 3,3'-ureylenebis-[6-(2-amino-8-hydroxy-6-sulfo-1-naphthylazo)]benzenesulfonic acid, tetrasodium salt (chlorazol fast pink), heparin and a sulphated dextran have been reported to have an anticomplementary effect, British Journal of Experimental Pathology, 33, 327–339 (1952). The compound 8-(3-benzamido-4-methylbenzamido)naphthalene-1, 3,5-trisulfonic acid (Suramin) is described as a competitive inhibitor of the complement system, Clin. Exp. Immunol., 10, 127–138 (1972). German Pat. No. 2,254,893 or South African Pat. No. 727,923 discloses certain 1-(diphenylmethyl)-4 -(3-phenylallyl)piperazines useful as complement inhibitors. Other chemical compounds having complement inhibiting activity are disclosed in, for example, Journal of Medicinal Chemistry, 12, 415–419; 902–905; 1049–1052; 1053–1056 (1969); Canadian Journal of Biochemistry, 47, 547–552 (1969); The Journal of Immunology, 93, 629–640 (1964); The Journal of Immunology, 104, 279–288 (1970); The Journal of Immunology, 106, 241–245 (1971); and The Journal of Immunology, 111, 1061–1066 (1973).

It has been reported that the known complement inhibitors epsilon-aminocaproic acid, Suramin and tranexamic acid all have been used with success in the treatment of hereditary angioneurotic edema, a disease state resulting from an inherited deficiency or lack of function of the serum inhibitor of the activated first component of complement (C1 inhibitor), The New England Journal of Medicine, 286, 808–812 (1972). It has also been reported that the drug, pentosan-poly-sulfoester, has an anticomplementary activity on human serum both in vitro and in vivo, as judged by the reduction in the total hemolytic complement activity; Pathologie Biologie, 25, 33–36 (1977).

The compounds of the present invention may be administered internally, e.g., orally, intra-articularly or parenterally e.g., intra-articular, to a warm-blooded animal to inhibit complement in the body fluid of the animal, such inhibition being useful in the amelioration or prevention of those reactions dependent upon the function of complement, such as inflammatory process and cell membrane damage induced by antigen-antibody complexes. A range of doses may be employed depending on the mode of administration, the condition being treated and the particular compound being used. For example, for intravenous or subcutaneous use from about 5 to about 50 mg/kg/day, or every 6 hours for more rapidly excreted salts, may be used. For intra-articular use for large joints such as the knee, from about 2 to about 20 mg/joint per week may be used, with proportionally smaller doses for smaller joints. The dosage range is to be adjusted to provide optimum therapeutic response in the warm-blooded animal being treated. In general, the amount of compound administered can vary over a wide range to provide from about 5 mg/kg to about 100 mg/kg of body weight of animal per day. The usual daily dosage for a 70 kg subject may vary from about 350 mg to about 3.5 g. Unit doses of the acid or salt can contain from about 0.5 mg to about 500 mg.

While in general the sodium salts of the acids of the invention are suitable for parenteral use, other salts may also be prepared, such as those of primary amines, e.g., ethylamine; secondary amines, e.g., diethylamine or diethanol amine; tertiary amines, e.g., pyridine or triethylamine or 2-dimethylaminomethyl-dibenzofuran; aliphatic diamines, e.g., decamethylenediamine; and aromatic diamines, can be prepared. Some of these are soluble in water, others are soluble in saline solution, and still others are insoluble and can be used for purposes of preparing suspensions for injection. Furthermore as well as the sodium salt, those of the alkali metals, such as potassium and lithium; of ammonia; and of the alkaline earth metals, such as calcium or magnesium, may be employed. It will be apparent, therefore, that these salts embrace, in general derivatives of salt-forming cations.

In therapeutic use, the compounds of this invention may be administered in the form of conventional pharmaceutical compositions. Such compositions may be formulated so as to be suitable for oral or parenteral administration. The active ingredient may be combined in admixture with a pharmaceutically acceptable carrier, which carrier may take a wide variety of forms depending on the form of preparation desired for administration, i.e., oral or parenteral. The compounds can be used in compositions such as tablets. Here, the principal active ingredient is mixed with conventional tabletting ingredients such as corn starch, lactose, sucrose, sorbitol, talc, stearic acid, magnesium stearate, dicalcium phosphate, gums, or similar materials as non-toxic pharmaceutically acceptable diluents or carriers. The tablets or pills of the novel compositions can be laminated or otherwise compounded to provide a dosage form affording the advantage of prolonged or delayed action or predetermined successive action of the enclosed medication. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids or mixtures or polymeric acids with such materials as shellac, shellac and cetyl alcohol, cellulose acetate and the like. A particularly advantageous enteric coating comprises a styrene maleic acid copolymer together with known materials contributing to the enteric properties of the coating. The tablet or pill may be colored through the use of an appropriate non-toxic dye, so as to provide a pleasing appearance.

The liquid forms in which the novel compositions of the present invention may be incorporated for administration include suitable flavored emulsions with edible oils, such as, cottonseed oil, sesame oil, coconut oil, peanut oil, and the like, as well as elixirs and similar pharmaceutical vehicles. Sterile suspensions or solutions can be prepared for parenteral use. Isotonic preparations containing suitable preservatives are also desirable for injection use.

The term dosage form, as described herein, refers to physically discrete units suitable as unitary dosage for warm-blooded animal subjects, each unit containing a predetermined quantity of active component calculated to produce the desired therapeutic effect in association with the required pharmaceutical diluent, carrier or vehicle. The specification for the novel dosage forms of this invention are indicated by characteristics of the active component and the particular therapeutic effect to be achieved or the limitations inherent in the art of compounding such an active component for therapeutic use in warm-blooded animals as disclosed in this specification. Examples of suitable oral dosage forms in accord with this invention are tablets, capsules, pills, powder packets, granules, wafers, cachets, teaspoonfuls, dropperfuls, ampules, vials, segregated multiples of any of the foregoing and other forms as herein described.

The complement inhibiting activity of the compounds of this invention has been demonstrated by one or more of the following identified tests: (i) Test, Code 026 (C1 inhibitor) — This test measures the ability of activated human C1 to destroy fluid phase human C2 in the presence of C4 and appropriate dilutions of the test compound. An active inhibitor protects C2 from C1 and C4; (ii) Test, Code 035 (C3–C9 inhibitor) — This test determines the ability of the late components of human complement (C3–C9) to lyse EAC 142 in the presence of appropriate dilutions of the test compound. An active inhibitor protects EAC 142 from lysis by human C3–C9; (iii) Test, Code 036 (C-Shunt inhibitor) — In this test human erythrocytes rendered fragile are lysed in autologous serum via the shunt pathway activated by cobra venom factor in the presence of appropriate dilutions of the test compound. Inhibition of the shunt pathway results in failure of lysis; (iv) Forssman Vasculitis Test — Here, the well known complement dependent lesion, Forssman vasculitis, is produced in guinea pigs by intradermal injection of rabbit anti-Forssman antiserum. The lesion is measured in terms of diameter, edema and hemorrhage and the extent to which a combined index of these is inhibited by prior intraperitoneal injection of the test compound at 200 mg/kg is then reported, unless otherwise stated; (v) Forssman Shock Test — Lethal shock is produced in guinea pigs by an i.v. injection of anti-Forssman antiserum and the harmonic mean death time of treated guinea pigs is compared with that of simultaneous controls; (vi) Complement Level Reduction Test — In this test, the above dosed guinea pigs, or others, are bled for serum and the complement level is determined in undiluted serum by the capillary tube method of U.S. Pat. No. 3,876,376 and compared to undosed control guinea pigs; and (vii) Cap 50 Test — Here, appropriate amounts of the test compound are added to a pool of guinea pig serum in vitro, after which the undiluted serum capillary tube assay referred to above is run. The concentration of compound inhibiting 50% is reported.

With reference to Table I, guinea pigs weighing about 300 g were dosed intravenously (i.v.) or intraperitoneally (i.p.) with 200 mg/kg of the test compound dissolved in saline and adjusted to pH 7–8. One hour after dosing, the guinea pigs were decapitated, blood was collected and the serum separated. The serum was tested for whole complement using the capillary tube assay. Percent inhibition was calculated by comparison with simultaneous controls. The results appear in Table I together with results of tests, code 026, 035, 036, Cap 50, % inhibition and Forssman shock. Table I shows that the compounds of the invention possess highly significant in vitro and in vivo, complement inhibiting activity in warm-blooded animals.

TABLE I
Biological Activities

| Compound | C1 026* Wells | C-Late 035* Wells | Shunt Inhibition 036* Wells | Cap 50* | In Vivo Activity (Guinea Pig) % Inhibition | | | | | |
|---|---|---|---|---|---|---|---|---|---|---|
| | | | | | Intraperitoneal Time (min) | | | Intravenous Time (min) | | |
| | | | | | 30 | 60 | 120 | 2 | 30 | 120 |
| 8-3-[3,5-Bis(3,6,8-trisulfo-1-naphthylcarbamoyl)phenyl]-2-thioureido-1,3,6-naphthalenetrisulfonic acid nonasodium salt | +7** +6 | +1** +1 | +1** +3 | 78 | −50 | −57 | −74 | −97 | −79 | −58 |
| 5,5′-5-[2-Thio-3-(3,6,8-trisulfo-1-naphthyl)ureido]-1,3-phenylene-bis(carbonylimino) diisophthalic acid heptasodium salt | +5 | N | +1 | | | | | | | |

*Code designation for tests employed as referred herein.
**Activity in wells a serial dilution assay. Higher well number indicates higher activity. The serial dilutions are two-fold.
N=Negative

EXAMPLE 1

8-{3-[3,5-Bis(3,6,8-trisulfo-1-naphthylcarbamoyl)phenyl]-2-thioureido}-1,3,6-naphthalenetrisulfonic acid nonasodium salt To a stirred solution of 32.0 g of 8-amino-1,3,6-naphthalenetrisulfonic acid trisodium salt in 350 ml of water plus 7.0 ml of concentrated hydrochloric acid, at room temperature, is added 10 g of thiophosgene. The mixture is stirred for 2½ hours, and treated with activated charcoal and filtered through diatomaceous earth. The filtrate is neutralized with 46 ml of 5N sodium hydroxide then is concentrated, cooled to room temperature and filtered. The product is washed with a small amount of ice-water, then acetone and ether to give 13.7 g of material. Further concentration of the filtrate yields another 13.8 of product. The product fractions (27.5 g) are combined and recrystallized from 40 ml of water. The product is collected, washed with ice-water, acetone and ether and dried by conventional means to give 11.2 g of 8-isothiocyanato-1,3,6-naphthalenetrisulfonic acid trisodium salt.

A mixture of 60.0 g of 5-nitroisophthalic acid, 300 ml of thionyl chloride and one ml of dimethylformamide is stirred at room temperature for 30 minutes, then is refluxed for one hour. The resulting clear solution is allowed to stand 24 hours then is evaporated to a small volume in vacuo. The evaporation step is then repeated with toluene and the resulting liquid is diluted with 250 ml of hexane. The mixture is stirred and cooled until the resulting oil is solidified. The product is ground to a powder and is recrystallized twice from carbon tetrachloride to give 47.4 g of 5-nitroisophthaloyl chloride.

To a solution of 13.75 g of 8-amino-1,3,6-naphthalenetrisulfonic acid trisodium salt and 4.6 g of sodium acetate trihydrate in 100 ml of water in a 500 ml baffle flask is added 4.10 g of powdered 5-nitroisophthaloyl chloride. The mixture is stirred vigorously at room temperature for one hour then is filtered through diatomaceous earth. The filtrate is concentrated to 50 ml, then warmed, acidified with 0.5 ml of concentrated hydrochloric acid and diluted with 50 ml of hot ethanol. The product is crystallized on cooling with scratching and is collected by filtration, then washed with 25 ml of 55% aqueous ethanol and 60 ml of ethanol. Additional product is obtained from the filtrate in the same manner. The total product is dried by conventional means to give 13.8 g of 8,8'-[(5-nitro-1,3-phenylene)bis(carbonylimino)]-di-1,3,6-naphthalenetrisulfonic acid hexasodium salt.

A mixture of 4.45 g of the preceding compound, 0.5 g of 10% palladium on carbon catalyst and 50 ml of water is hydrogenated in a Parr shaker at room temperature for one hour. The mixture is filtered through diatomaceous earth and the filtrate containing 8,8'-[(5-amino-m-phenylene)bis(carbonylimino)]-di-1,3,6-naphthalenetrisulfonic acid hexasodium salt is concentrated to 25 ml. To this solution is added 2.04 g of 8-isothiocyanato-1,3,6-naphthalenetrisulfonic acid trisodium salt with standing for 23 hours. The solution is diluted with 100 ml of ethanol to give a precipitate which is filtered and washed with 80% aqueous ethanol, ethanol and ether, then is dried overnight by conventional means to give 5.8 g of the product of the example as a yellow powder.

EXAMPLE 2

5,5'-{{5-[2-Thio-3-(3,6,8-trisulfo-1-naphthyl)ureido]-1,3-phenylene}bis(carbonylimino)}diisophthalic acid heptasodium salt A mixture of 21.1 g of 5-nitroisophthalic acid, 40.5 ml of 5N sodium hydroxide and 2.0 g of 10% palladium on carbon catalyst in 110 ml of water is hydrogenated at room temperature for 1 hour and then filtered through diatomaceous earth. To the solution of 5-aminoisophthalic acid disodium salt is added 9.2 g of sodium bicarbonate followed by 13.65 g of powdered 5-nitroisophthaloyl chloride (prepared as described in Example 1). The solution is cooled in a water bath and stirred vigorously in a baffle flask for 1 hour and 15 minutes. The mixture is filtered, the filtrate is concentrated to approximately 125 ml and 200 ml of ethanol is added to give a yellow precipitate. The mixture is filtered and the product is washed with 66% aqueous ethanol, ethanol and ether. The material is dried, then dissolved in 200 ml of water. The solution is filtered through diatomaceous earth and diluted slowly with stirring and warming with 300 ml of ethanol. The precipitate formed is collected and washed with 100 ml of 60% aqueous ethanol, 400 ml of ethanol and ether. The product is dried by conventional means to give 27.8 g of 5,5'-[5-nitro-1,3-phenylenebis(carbonylimino)]diisophthalic acid tetrasodium salt.

A mixture of 25.0 g of the product above and 2.5 g of 10% palladium on carbon catalyst in 150 ml of water is hydrogenated in a Parr shaker at room temperature for 1½ hours. The resulting mixture is filtered through diatomaceous earth. The filter is washed with 25-30 ml of water and the filtrate is diluted with 300 ml of ethanol with vigorous stirring. The precipitate formed is collected by filtration, washed with 60% aqueous ethanol, ethanol and ether and dried by conventional means to yield 22.2 g of 5,5'-[5-amino-1,3-phenylenebis(carbonylimino)]diisophthalic acid tetrasodium salt as a pale yellow powder.

To a solution of 2.55 g of 8-isothiocyanato-1,3,6-napthalenetrisulfonic acid trisodium salt (prepared as described in Example 1) in 15 ml of water is added 3.25 g of the preceding compound in 25 ml of water with stirring. Stirring is continued at room temperature for 18 hours. The solution is filtered and concentrated. The precipitate is dissolved in 30 ml of hot water and is slowly added to 60 ml of ethanol, with stirring, with formation of a precipitate. The mixture is allowed to cool and the precipitate is collected, washed with 80% aqueous ethanol, ethanol and ether and dried. The product is recrystallized from 40:60, water:ethanol, washed with ethanol and ether and dried to yield 1.7 g of the product of the example as a light yellow solid.

EXAMPLE 3

Preparation of Compressed Tablet

| Ingredient | mg/Tablet |
| --- | --- |
| Active Compound | 0.5-500 |
| Dibasic Calcium Phosphate N.F. | qs |
| Starch USP | 40 |
| Modified Starch | 10 |
| Magnesium Stearate USP | 1-5 |

EXAMPLE 4

Preparation of Compressed Tablet — Sustained Action

| Ingredient | mg/Tablet |
| --- | --- |
| Active Compound as Aluminum Lake*, Micronized | 0.5-500 (as acid equivalent) |
| Dibasic Calcium Phosphate N.F. | qs |
| Alginic Acid | 20 |
| Starch USP | 35 |
| Magnesium Stearate USP | 1-10 |

*Complement inhibitor plus aluminum sulfate yields aluminum complement inhibitor. Complement inhibitor content in aluminum lake ranges from 5-30%.

EXAMPLE 5

Preparation of Hard Shell Capsule

| Ingredient | mg/Capsule |
| --- | --- |
| Active Compound | 0.5-500 |
| Lactose, Spray Dried | qs |
| Magnesium Stearate | 1-10 |

EXAMPLE 6

Preparation of Oral Liquid (Syrup)

| Ingredient | mg/Capsule |
| --- | --- |
| Active Compound | 0.05-5 |
| Liquid Sugar | 75.0 |
| Methyl Paraben USP | 0.18 |
| Propyl Paraben USP | 0.02 |
| Flavoring Agent | qs |
| Purified Water qs ad | 100.0 |

EXAMPLE 7

Preparation of Oral Liquid (Elixir)

| Ingredient | % W/V |
|---|---|
| Active Compound | 0.05–5 |
| Alcohol USP | 12.5 |
| Glycerin USP | 45.0 |
| Syrup USP | 20.0 |
| Flavoring Agent | qs |
| Purified Water qs ad | 100.0 |

EXAMPLE 8

Preparation of Oral Suspension (Syrup)

| Ingredient | % W/V |
|---|---|
| Active Compound as Aluminum Lake, Micronized | 0.5–5 (acid equivalent) |
| Polysorbate 80 USP | 0.1 |
| Magnesium Aluminum Silicate, Colloidal | 0.3 |
| Flavoring Agent | qs |
| Methyl Paraben USP | 0.18 |
| Propyl Paraben USP | 0.02 |
| Liquid Sugar | 75.0 |
| Purified Water qs ad | 100.0 |

EXAMPLE 9

Preparation of Injectable Solution

| Ingredient | % W/V |
|---|---|
| Active Compound | 0.05–5 |
| Benzyl Alcohol N.F. | 0.9 |
| Water for Injection | 100.0 |

EXAMPLE 10

Preparation of Injectable Oil

| Ingredient | % W/V |
|---|---|
| Active Compound | 0.05–5 |
| Benzyl Alcohol | 1.5 |
| Sesame Oil qs ad | 100.0 |

EXAMPLE 11

Preparation of Intra-Articular Product

| Ingredient | Amount |
|---|---|
| Active Compound | 2–20 mg |
| NaCl (physiological saline) | 0.9% |
| Benzyl Alcohol | 0.9% |
| Sodium Carboxymethylcellulose | 1–5% |
| pH adjusted to 5.0–7.5 | |
| Water for Injection qs ad | 100% |

EXAMPLE 12

Preparation of Injectable Depo Suspension

| Ingredient | % W/V |
|---|---|
| Active Compound | 0.05–5 (acid equivalent) |
| Polysorbate 80 USP | 0.2 |
| Polyethylene Glycol 4000 USP | 3.0 |
| Sodium Chloride USP | 0.8 |
| Benzyl Alcohol N.F. | 0.9 |
| HCl to pH 6–8 | qs |
| Water for Injection qs ad | 100.0 |

We claim:

1. A compound of the formula:

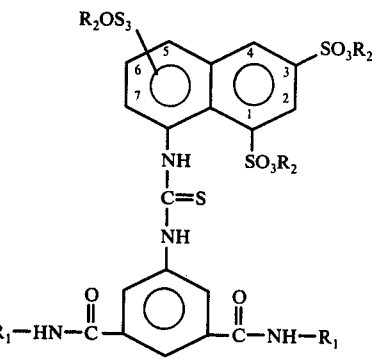

wherein $R_1$ is selected from the group consisting of

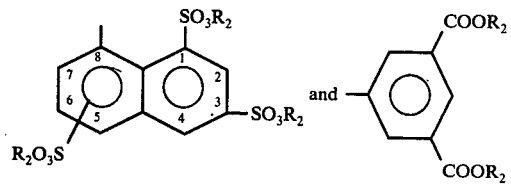

wherein $R_2$ is selected from the group consisting of alkali metal; and the pharmaceutically acceptable salts thereof.

2. A compound according to claim 1, wherein $R_1$ is selected from the group consisting of

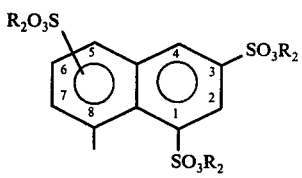

wherein $R_2$ is as previously defined.

3. The compound according to claim 1, 8- 3-[3,5-bis(3,6,8-trisulfo-1-naphthylcarbamoyl)phenyl]-2-thioureido-1,3,6-naphthalenetrisulfonic acid nonasodium salt.

4. The compound according to claim 1, 5,5'- 5-[2-thio-3-(3,6,8-trisulfo-1-naphthyl)ureido]-1,3-phenylene bis-(carbonylimino) diisophthalic acid heptasodium salt.

* * * * *